United States Patent
Pearson et al.

(12) 
(10) Patent No.: US 6,359,007 B1
(45) Date of Patent: Mar. 19, 2002

(54) CLINICAL USES FOR L-ARGININE ASCORBATE AND VARIOUS METALLOARGINATE COMPLEXES

(75) Inventors: Don C. Pearson, Lakewood, WA (US); Kenneth T. Richardson, Anchorage, AK (US)

(73) Assignee: ChronoRX, LLC, Anchorage, AK (US)

( * ) Notice: Subject to any disclaimer, the term of this patent is extended or adjusted under 35 U.S.C. 154(b) by 0 days.

(21) Appl. No.: 09/534,909

(22) Filed: Mar. 23, 2000

Related U.S. Application Data

(60) Provisional application No. 60/128,155, filed on Apr. 7, 1999.

(51) Int. Cl.[7] .............................................. A61K 31/195
(52) U.S. Cl. ....................................................... 514/565
(58) Field of Search .......................................... 514/565

(56) References Cited

U.S. PATENT DOCUMENTS

| | | | | |
|---|---|---|---|---|
| 5,217,997 A | * | 6/1993 | Levere et al. ................ | 514/565 |
| 5,780,039 A | * | 7/1998 | Greenberg et al. .......... | 424/400 |

FOREIGN PATENT DOCUMENTS

| | | | |
|---|---|---|---|
| ES | 349502 | * | 8/1969 |

OTHER PUBLICATIONS

Johnson et al., Arch. Ophth. (108, No. 2, 259–263) (abstract), 1990.*
Adams et al., *Atherosclerosis* (1997) 129(2):261–9.
Bettger, *Canadian J. of Physiology & Pharmacology* (1993) 71(9):721–4.
Boger et al., *Circulation* (1997) 96(4): 1282–90.
do Carmo et al., *Gen. Pharmacol.* (1998) 30(3): 319–24.
Garini et al., *Recenti Prog. Med.* (1997) 88(2): 90–9.
Gold et al., *Am. J. Physiol.* (1990) 259(6 Pt 2): H1813–21.
Haeffliger et al., *Survey of Ophthalmology* (1994) 39(2): 123–32 cxf 23.
Kraus et al., *J. Nutr.* (1997) 127(7): 1290–6.
Luscher et al., *J. Human Hypertension* (1992) 6(Suppl 2): S3–8.
Orgul et al., *J. Glaucoma* (1996) 5(2): 135–8.
Reinhart, *Arch. Intern. Med.* (1988) 148(11): 2415–20.
Schuschke, *J. Nutr.* (1997) 127(12): 2274–81 cxf 423.
Uhlmann et al., *Eur. Surg. Res.* (1998) 30(3): 175–84.

* cited by examiner

*Primary Examiner*—Phyllis G. Spivack
(74) *Attorney, Agent, or Firm*—Townsend and Towsend and Crew LLP

(57) ABSTRACT

Various clinical uses for L-arginine complexes are presented. The active agents have individual and complementary physiological functions especially as these relate to conditions and functions, which influence endothelial biochemistry and physiology. The active components of the invention are selected for inclusion in unique combinations that will clinically reduce risks of vasculopathy in various diseases. The reduction of endothelial dysfunctional risks, often associated with aging and generalized poor vascular health and function, will maximize the potential clinical therapeutic success of other mediations and concurrently avoid some risks of pharmaceutical side effects.

2 Claims, No Drawings

CLINICAL USES FOR L-ARGININE ASCORBATE AND VARIOUS METALLOARGINATE COMPLEXES

CROSS REFERENCE TO RELATED APPLICATION

This application is related to United States Provisional Patent Application No. 60/128,155, filed Apr. 7, 1999, and claims all benefits legally available therefrom. Provisional Patent Application No. 60/128,155 is hereby incorporated by reference for all purposes capable of being served thereby.

BACKGROUND OF THE INVENTION

1. Field of the Invention

This invention relates to the identification of clinical uses of compounds that include L-arginine and various biologically available metalloarginates. In particular, the invention comprises L-arginine, magnesium L-arginate, zinc L-arginate, and copper L-arginate with their ascorbate salts, and their uses as oral nutritional supplements and clinical agents.

2. Description of the Prior Art (a) L-Arginine and Nitric Oxide (NO)

L-arginine is the precursor amino acid critical to the synthesis of nitric oxide by nitric oxide synthase (cNOS or eNOS), the enzyme responsible for constitutive production of NO by vascular endothelial and neural cells.

Vascular endothelial dysfunction secondary to endothelial stress, ischemia, atherosclerosis, hypertension, aging, diabetes or other etiologies, results in a reduction of the production of NO. Endothelial dysfunction has been well documented in the coronary circulation, and probably also the renal circulation, of patients with essential hypertension and, because of the reduced production of local levels of cNOS, aging alone or aging accompanied by atherosclerosis of the vascular endothelium reduce its ability to produce NO.

NO increases local vascular levels of guanosine 3',5'-cyclic monophosphate (cGMP), by providing the molecular radical necessary for the production of cGMP via the enzyme guanylate cyclase. Adequate cGMP results in: increased local blood flow, increased smooth muscle relaxation, increases in healthy endothelial cell proliferation, reduced endothelial permeability, inhibition of vascular smooth muscle cell (VSMC) proliferation, inhibition of cellular (both neural and glial) apoptosis and useful alterations in the ciliary muscle and trabecular meshwork of the eye which result in improvements in outflow facility.

There is some evidence that NO alone (also see magnesium, below) modulates intracellular calcium ($Ca^{+2}$) oscillations by blocking endoplasmic reticular $Ca^{+2}$ release and by enhancing intracellular $Ca^{+2}$ extrusion.

NO is not only helpfully antithrombotic, it also strongly counters the potent endothelial-derived vasoconstrictor, endothelin-1 (ET-1). A fine balance of NO and ET-1 not only mediates local blood flow but also many facets of systemic vascular autoregulation. If NO is reduced, an unopposed tonic, ET-1-induced vasoconstrictive response occurs.

Plasma levels of L-arginine can be increased by oral administration. In young men with coronary artery disease, oral L-arginine has been shown to improve endothelium-dependent dilatation and reduce monocyte/endothelial cell adhesion. Dietary L-arginine improves NO-dependent vasodilator function in cholesterol-fed rabbits and blocks the progression of aortic plaques (see below). This apparently occurs via the restoration of cNOS and a reduction of vascular oxidative stress. Plasma arginine concentration is reduced in diabetic rats but is restored to normal following dietary L-arginine supplementation.

Oral doses of L-arginine raise levels of available NO. In one study, chronic administration of L-arginine (2% in drinking water) appeared to improve endothelium-dependent vasodilator function and systemic NO production and to reduce vascular oxidative stress in cholesterol-fed rabbits with pre-existing hypercholesterolemia.

(b) Magnesium ($Mg^{+2}$)

$Mg^{+2}$ deficiencies are widespread in the general population. This is especially true in diabetic patients with normal renal function, in the institutionalized elderly, in chronic alcoholics and smokers, and in populations living in regions with water supplies low in $Mg^{+2}$.

$Mg^{+2}$ deficiency has been associated with cardiac arrythmias, hypertension, decreased vascular intraluminal fluidity and vasoconstriction. These pathologies result from a reduction in the efficiency of the modulation of cell membrane $Ca^{+2}$ channel gating. By a variety of mechanisms, $Mg^{+2}$ modulates the level of both intracellular and extracellular $Ca^{+2}$. Excess cytoplasmic free $Ca^{+2}$ has the deleterious effect of leading to an increase in ET-1, with its associated increase in vasoconstriction and cell apoptosis. $Mg^{+2}$ optimizes cytoplasmic free $Ca^{+2}$ levels without interfering with normal $Ca^{+2}$ intracellular signaling. Because vascular endothelial production of ET-1 is highly dependent upon cytosolic $Ca^{+2}$ influx via transmembrane $Ca^{+2}$ channels, $Ca^{+2}$ channel blockade reduces this influx and reduces the production of ET-1.

The eye maintains the equilibrium of intraocular pressure by a dynamic balance between aqueous humor production and aqueous outflow via the trabecular meshwork. If outflow is reduced intraocular pressure rises, and vice versa. Levels of ET-1 are elevated in the aqueous humor of patients with chronic open angle glaucoma, and local production of cNOS is reduced in these eyes. Induced elevations of aqueous ET-1 levels produce optic nerve collapse in rabbits and monkeys. The same critical vasoactive balance between ET-1 and NO appears to be as important in regulating vascular flow within the eye as it is in regulating systemic blood flow. Imbalances that result in uncontested activity of ET-1 because of reduced levels of NO, are strongly implicated in the vascular progression of visual field loss associated with chronic glaucoma.

In addition to these vascular effects, trabecular smooth muscle contraction is produced by ET-1 and strongly opposes the tonic, relaxation properties of NO. As a result, trabecular contraction in the eye is stimulated, resistance to aqueous outflow is increased and IOP increases. At the same time this pressure increase is occurring, putative vasoconstriction of the small vessels of the optic nerve (probably the posterior ciliary arteries) occurs, and the course is set for optic nerve atrophy and blindness.

Clinical confirmation of these findings is found in the fact that exposure of patients to vasodilating stimuli or to $Ca^{+2}$ channel blockers has resulted in an improvement of the glaucomatous visual field; a serendipitous reduction of IOP has been observed as a side effect in glaucoma patients using $Ca^{+2}$ channel blockers for systemic hypertension. Unfortunately, pharmaceutical $Ca^{+2}$ channel blockers used clinically at effective doses have gross, amplitude driven, essentially uncontrolled effects on $Ca^{+2}$ cellular signaling. As a result, prescribing pharmaceutical doses of blockers to systemically normotensive glaucoma patients subjects the glaucomatous optic nerve to a significant risk of hypoxia secondary to reduced perfusion pressure and leads to an increased risk of visual loss. The sensitive ability of $Mg^{+2}$ to optimize cytoplasmic free $Ca^{+2}$ levels permits more delicate control of the modulation of ET-1/NO balances without interfering with normal $Ca^{+2}$ intracellular signaling and avoids the risks associated with iatrogenic hypotension.

The correction of an existing $Mg^{+2}$ deficiency exerts counter-apoptotic, antihypertensive, anti-atherosclerotic, anti-arrhythmic, antithrombotic effects and result in a reduction in the risk of visual loss in chronic glaucoma. The prophylactic nutritional supplementation of $Mg^{+2}$ that prevents the development of magnesium deficiencies, particularly in identifiable groups, will reduce the risks associated with hypomagnesemia and avoid the undesirable side effects associated with powerful $Ca^{+2}$ channel blockers.

(c) Zinc ($Zn^{+2}$) and Copper ($Cu^{+2}$)

$Zn^{+2}$ and $Cu^{+2}$ are cofactors for, and are reported to be inducers of, the antioxidant superoxide dismutase (CuZnSOD). $Zn^{+2}$ also binds the sulfhydryl groups of proteins, additionally protecting them from oxidation.

CuZnSOD enzymatically degrades the free radical superoxide ($O^{\cdot}$). Although $O^{\cdot}$ itself is not as damaging to cell membranes as other free radicals, it spawns the highly toxic hydroxyl radical ($OH^-$) via a Fenton reaction with iron. Because constitutively produced NO (from cNOS) is readily inactivated by $O^{\cdot}$, the bioactivity of this endothelium-derived NO is dependent on the local availability and activity of CuZnSOD. In addition, $O^{\cdot}$ interacts with excessive, macrophage-generated (Type II iNOS-derived) NO in inflamed or irritated tissues and generates peroxynitrite, a long-lived and highly reactive oxygen species which is implicated in coronary atherosclerosis. Tyrosine nitration of this peroxynitrite causes endothelial dysfunction by disrupting the integrity of the cell membrane. This peroxynitrite is also implicated in the caspase cascade leading to apoptosis in neurologic conditions. CuZnSOD protects against potentially harmful effects that may be associated with excessive levels of Type II iNOS-generated NO. In addition, there is some evidence that CuZnSOD may alleviate retinal lesions caused by intraocular pressure elevation.

$Zn^{+2}$-deficient rats develop increased erythrocyte fragility and reduced CuZnSOD activity. They are particularly vulnerable when the metal deficiency is combined with a deficiency of anti-oxidants.

Appropriate dietary $Cu^{+2}$ is essential for cardiovascular homeostasis. Cytosolic CuZnSOD is inactivated in diets deficient in $Cu^{+2}$. Studies of tissue microcirculation demonstrate that $Cu^{+2}$ is important in mechanisms of macromolecular leakage, platelet-endothelial interactions and vascular smooth muscle reactivity. These abnormalities are not surprising in view of the role of CuZnSOD and NO in maintaining vascular integrity. Dietary $Cu^{+2}$ appears to be necessary for several microvascular control mechanisms affecting the regulation of peripheral blood flow; NO-mediated arteriole vasodilation is compromised in copper-deficiency. Functional deficits of NO can be reversed by the dietary addition of CuZnSOD, suggesting that degradation of NO by $O^{\cdot}$ may occur during $Cu^{+2}$ deprivation.

Although seemingly not uncommon, dietary deficiencies of these two cofactors, $Zn^{+2}$ and $Cu^{+2}$, should be avoided.

(d) Ascorbate (ascorbic acid, vitamin C)

Ascorbic acid (AA) is a powerful antioxidant, a cofactor in collagen synthesis, affects platelet activation and prostaglandin synthesis, and inhibits the polyol (sorbitol) pathway. In diabetics or patients with insulin resistance, net circulating concentrations of AA are reduced because the cellular uptake of ascorbate is promoted by insulin; because the cellular uptake of AA is concurrently reduced by hyperglycemia, there is a secondary, excessive excretion by the diabetic kidney.

AA improves impaired acetylcholine-induced vasodilation by mechanisms linked to NO formation.

AA may mimic glutathione in the stimulation of CuZnSOD. As a substitute, free standing and powerful free radical scavenger, it preserves constitutive levels of glutathione.

AA phase transfer rejuvenation of α-tocopherol maintains and amplifies the latter's chain-breaking effect on lipid peroxidation, and similarly complements α-lipoic acid; α-tocopherol and α-lipoic acid constitute the ultimate protection from free radical damage to cell membranes—especially those of the vascular endothelium.

SUMMARY OF THE INVENTION

Metal L-arginine complexes used in the practice of certain embodiments of this invention have the following formula:

$$(Arg) \, M \, X$$

in which:

The symbol "Arg" represents the amino acid L-arginine or bis-L-arginine;

M is either $Mg^{+2}$, $Cu^{+2}$ or $Zn^{+2}$; and

X is either hydroxide, halide, sulfate, phosphate, acetate, ascorbate or bis-ascorbate.

Other embodiments of this invention involve the use of non-metal-containing L-arginate complexes of the formula $$(Arg) \, X$$

in which:

Arg is either L-arginine or bis-L-arginine; and

X is either hydroxide, halide, sulfate, phosphate, acetate, ascorbate or bis-ascorbate.

In certain aspects, this invention resides in a method for the oral administration of L-arginine ascorbate or metalloarginate complexes, alone or in combination, as a nutrient for humans. The cation of the metalloarginate complexes may be $Mg^{+2}$, $Cu^{+2}$ or $Zn^{+2}$. In other aspects, the invention resides in a method for the oral administration of L-arginine ascorbate, bis-L-arginine ascorbate, or L-arginine bis-ascorbate, either alone or in combination, for the same purposes.

The compound is preferably administered in an oral daily dosage with preferred and most preferred amounts of the individual components as shown below.

| | Dosages in Milligrams | |
| --- | --- | --- |
| | Preferred | Most Preferred |
| L-arginine | 75 to 3125 | 250 to 1250 |
| Ascorbate | 75 to 2500 | 250 to 1000 |
| Copper | 0.15 to 7.5 | 0.5 to 3 |
| Magnesium | 30 to 1000 | 100 to 400 |
| Zinc | 1.5 to 125 | 5 to 50 |

Embodiments of the invention include administration in unit dosage forms that include tablets, capsules, powders, suspensions and liquids. The invention contemplates delivery vehicles of, among others, timed release, sustained release, controlled release, or zero-order release in substantially homogeneous or in coated bilayered release unit dosage forms with differential dissolution rates.

The present invention provides for the clinical use of defined arginate complexes which provide concurrent, pharmacologically appropriate dosage forms and amounts of L-arginine, $Mg^{+2}$, $Cu^{+2}$, $Zn^{+2}$ and ascorbate for the beneficial modification of conditions and functions either acutely or chronically associated with dysfunctional vascular endothelium or vasoconstriction, and for various clinical presentations adversely affected by dysfunctional vascular endothelium or vasoconstriction. It is particularly useful in any clinical diagnosis or finding in which it is important to ensure appropriate levels of cNOS, eNOS and NO.

DETAILED DESCRIPTION OF THE INVENTION AND PREFERRED EMBODIMENTS

All patents and published materials cited in this specification are incorporated herein by reference.

Definitions

All terms appearing in this specification and the appended claims are used in the same manner as commonly recognized among those skilled in the technology and terminology of pharmacology. These terms are therefore used in accordance with their conventional definitions, except as otherwise noted. Further clarifications of some of these terms as they apply specifically to this invention are offered below.

"Unit dosage form" refers to a composition intended for a single administration to a subject. Each unit dosage form typically comprises each of the active ingredients of this invention plus pharmaceutically acceptable excipients. Examples of unit dosage forms are individual tablets, individual capsules, bulk powders, and liquid solutions, emulsions or suspensions. The clinical condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

An "active agent" or "active ingredient" is a component of a dosage form that performs a biological function when administered or induces or affects (enhances or inhibits) a physiological process, condition or function in some manner. "Activity" is the ability to perform the function, or to induce or affect the process. Active agents and ingredients are distinguishable from excipients such as carriers, vehicles, diluents, lubricants, binders, and other formulating aids, and encapsulating or otherwise protective components.

"Delivery vehicle" is a composition, which comprises one or more active agents, and is designed to release the active agent in a particular fashion, either by immediately dispersing the agents in the digestive system, or by releasing the agents in a slow sustained fashion. The term encompasses porous microspheres, microcapsules, cross-linked porous beads, and liposomes that contain one or more active ingredients sequestered within internal cavities or porous spaces. The term also includes osmotic delivery systems, coated tablets or capsules that include nonporous microspheres, microcapsules, and liposomes, and active agents dispersed within polymeric matrices. A dosage form can include one or more delivery vehicles.

"Controlled" or "sustained" or "time release" delivery are equivalent terms that describe the type of active agent delivery that occurs when the active agent is released from a delivery vehicle at a rate that is capable of being ascertained and manipulated over a period of time, which is generally on the order of minutes, hours or days, typically ranging from about thirty minutes to about 3 days, rather than being dispersed immediately upon entry into the digestive tract or upon contact with gastric fluid. A controlled release rate can vary as a function of a multiplicity of factors. Factors influencing the rate of delivery in controlled release include the particle size, composition, porosity, charge structure, and degree of hydration of the delivery vehicle and the active ingredient(s), the acidity of the environment (either internal or external to the delivery vehicle), and the solubility of the active agent in the physiological environment, i.e., the particular location along the digestive tract.

"Vasoconstriction" is the reduction of the cross section of a blood vessel lumen, inhibiting the free flow of blood through the vessel. Vasoconstriction can arise from platelet agglutination, acute or chronic contraction of vascular muscular layers, deposits on or in the lumen wall or from the thickening of the wall due to excessive growth or proliferation of one or more of the wall layers.

The phrase "substantially homogeneous," when used to describe a formulation (or portion of a formulation) that contains a combination of components, means that the components, although each may be in particle or powder form, are fully mixed so that the individual components are not divided into discrete layers or form concentration gradients within the formulation.

Solubility and Gastrointestinal Absorption Characteristics

Ions, metals and biomolecules are absorbed through the gastrointestinal epithelium by a variety of mechanisms; some passively according to concentration gradients, others require active transport by membrane-bound protein molecules that may be distributed differently along the course of the gastrointestinal tract and which may be more or less selective. Some gastrointestinal absorption of ions, heavy metals or biomolecules may occur by more than one mechanism.

The mucus layer covering the surface of the gastrointestinal tract may act as a barrier to drug absorption; therefore, the self-diffusion coefficients of drugs with different physicochemical properties in gastrointestinal mucus are important considerations. The most important physicochemical characteristic influencing the diffusion coefficient of smaller molecules through gastrointestinal mucous appears to be their lipophilicity; molecular size appears to have more influence for larger peptide drugs. Electrical charge has only a minor effect on the diffusion coefficients across the intestinal barrier.

Some ions, heavy metals or biomolecules may enhance or inhibit the gastrointestinal absorption of others. Substantial data is not available at the present time regarding this competitive absorption. However, where it is available, the quantities listed in the final formulations of the invention take these absorption characteristics into account.

Absorption data are included when available, otherwise qualitative comments based on molecular structure are included.

a) L-arginine

Absorption: About 38%. Absorption is high in the upper three gastrointestinal regions. The least absorption is in the ileum.

Pharmacokinetics: The gastrointestinal uptake of dietary arginine when the stomach is in the "fed" state, is about 38%. The bioavailability of a closely related molecule, dDAVP (1-deamino-8-D-arginine vasopressin) has been shown to be significantly higher in the three upper GI regions in comparison to the three lower regions. In an earlier study the bioavailability of dDAVP after direct application to the gastric, duodenal and jejunal was similar to a tablet delivery. Absorption from the ileum was lower than expected and no preferential site of absorption was found.

b) $Mg^{+2}$

Absorption: $Mg^{+2}$ is actively transported in the ileum. Limited, passive diffusion of $Mg^{+2}$ exists throughout the entire intestine.

Pharmacokinetics: $Mg^{+2}$ is converted to magnesium chloride in the stomach. However there is a maximum bolus absorption of 8 meq of $Mg^{+2}$ per meal with a curvilinear falloff.

c) $Cu^{+2}$

Absorption: 30–40% of $Cu^{+2}$ absorption is via a carrier-mediated transport. Aging may decrease the efficiency of $Cu^{+2}$ homeostasis, resulting in higher plasma $Cu^{+2}$ concentrations in the elderly. However, there is a minimum dietary $Cu^{+2}$ requirement of 0.4 to 0.8 mg/day to replace daily losses of approximately 1.3 mg/day. Supplementation with inappropriate amounts of $Zn^{+2}$ has a detrimental effect on $Cu^{+2}$ levels.

Pharmacokinetics: The human gastrointestinal system can absorb 30–40% of ingested $Cu^{+2}$ from the typical diets consumed in industrialized countries. Experimental data support the existence of a carrier-mediated transport mechanism with an affinity constant in the micromolar range. Dietary supplements of minerals with similar chemical characteristics (e.g., iron or $Zn^{+2}$) can reduce $Cu^{+2}$ absorption. Proteins and soluble carbohydrates tend to improve $Cu^{+2}$ absorption and bioavailability by enhancing its solubility and intestinal bulk flow. Organic acids, other than ascorbic acid, or agents that form low-molecular-weight chelates, are likely to have a positive effect on overall $Cu^{+2}$ absorption. In order to maintain $Cu^{+2}$ balance, the average adult male must consume a diet which contains at least 2 mg $Cu^{+2}$/day, otherwise dietary $Cu^{+2}$ may fall below that required for plasma iron transport.

d) $Zn^{+2}$

Absorption: $Zn^{+2}$ absorption ranges from 40% to 86%. About 37% of ingested $Zn^{+2}$ enters the plasma. Gastrointestinal absorption is essentially complete by 4 hours. The duodenum and ileum are important sites for rapid $Zn^{+2}$ absorption. A continuous, slower absorption of $Zn^{+2}$ may take place in the jejunum while the stomach, cecum and colon appear to be insignificant sites of absorption. Fractional absorption is not affected by the quantity of $Zn^{+2}$ ingested until this exceeds 5 mg; mean plasma $Zn^{+2}$ increases about 37% above pre-load levels in face of an 11-fold increase in $Zn^{+2}$ intake.

Pharmacokinetics: $Zn^{+2}$ supplements reduce the ferroxidase activity of serum and the prooxidant activity of erythrocyte superoxide. A detrimental effect on $Cu^{+2}$ levels occurs after supplementation with inappropriate amounts of $Zn^{+2}$. $Zn^{+2}$ is necessary for nucleic acid and protein synthesis, the formation of sulfated molecules, and the formation of retinal reductase and CuZnSOD; the highest concentration of this trace element in the human body is measured in the eye, particularly in the pigment-containing components. $Zn^{+2}$ is required for the structure and activity of many ocular metalloenzymes. Although the exact mechanism of its molecular and cellular functions is poorly understood, the essentiality of this element in various component of the eye (including the retina, choroid, cornea and lens) is well established; $Zn^{+2}$ deficiency causes functional impairments in various parts of the eye. However, $Zn^{+2}$ related toxicities also have been shown in human and animal eyes.

e) Ascorbate (ascorbic acid, vitamin C)

Absorption: Natural and synthetic ascorbate is avidly absorbed in the first 30 cm of jejunum.

Pharmacokinetics: As the daily oral dose vitamin C is increased, the concentration of AA in the plasma and other body fluids does not increase proportionally, but approaches an upper limit. For example, when the daily dose is increased from 200 to 2500 mg, the mean steady state plasma concentration increases only from 12 to 15 mg/L as a result of sharply rising renal clearances. The analysis indicates that both saturable gastrointestinal absorption and nonlinear renal clearance additively produce a ceiling effect in plasma concentrations. As a consequence, there is no pharmacokinetic justification for the use of mega-doses of ascorbic acid. In fact, individuals with a history of kidney stone formation and those who experience iron overload (e.g., sickle cell anemia) should exercise caution before using supplemental vitamin C. (Vitamin C is a physiological factor essential for the absorption of dietary iron.) Recurrent renal stone-formers and patients with renal failure who have a defect in ascorbate or oxalate metabolism should restrict daily vitamin C intakes to approximately 100 mg.

Composition, Formulations and Dosages

Examples of L-arginine that are contemplated by the invention include L-arginine ascorbate, magnesium L-arginate, zinc L-arginate and copper L-arginate and their bis-L-arginine and bis-ascorbate forms.

In certain embodiments of the invention, the dosage form is a substantially homogeneous single layer tablet that releases all of its components into the stomach upon ingestion. In certain other embodiments of the invention, the dosage form is a tablet in which the active agents are protected by an acid-resistant coating for release only in the intestine, and optionally in a sustained-release manner over a period of time.

The dosage forms of this invention can be formulated for administration at rates of one or more unit dosage forms per day. Unit dosage forms to be taken three to four times per day for immediate release tablets are preferred. Unit dosage forms to be taken once or twice daily for controlled (sustained) release tablets are preferred.

The polymer matrix of the controlled (sustained) release tablet, having been given an enteric coating in the granulation process with EUDRAGIT, does not dissolve in the acid pH of the stomach, but remains intact until it passes to the upper part of the small intestine, where the enteric coating dissolves in the more alkaline environment of the intestine. The polymeric matrix then immediately begins to imbibe water from the intestinal fluid, forming a water-swollen gel. The agents incorporated into this layer are then available for intestinal absorption as they osmotically diffuse from the gel. The rate of diffusion the agent is reasonably constant for the useful life of the matrix (approximately four hours), by which time the incorporated agent is finally depleted and the matrix disintegrates. Such a single layer controlled release tablet, substantially homogenous in composition, is prepared as illustrated in the examples that follow.

The slower, more sustained release of the active agents can be achieved by placing the active agents in one or more delivery vehicles that inherently retard the release rate. Examples of such delivery vehicles are polymeric matrices that maintain their structural integrity for a period of time prior to dissolving, or that resist dissolving in the stomach but are readily made available in the post-gastric environment by the alkalinity of the intestine, or by the action of metabolites and enzymes that are present only in the intestine. The preparation and use of polymeric matrices designed for sustained drug release is well known. Examples are disclosed in U.S. Pat. No. 5,238,714 (Aug. 24, 1993) to Wallace et al.; Bechtel, W., Radiology 161: 601–604 (1986); and Tice et al., EPO 0302582, Feb. 8, 1989. Selection of the most appropriate polymeric matrix for a particular formulation can be governed by the intended use of the formulation. Preferred polymeric matrices are hydrophilic, water-swellable polymers such as hydroxymethylcellulose, hydroxypropylcellulose, hydroxyethylcellulose, hydroxymethylpropylcellulose, polyethylene oxide, and porous bioerodible particles prepared from alginate and chitosan that have been ionically crosslinked.

A delayed, post-gastric, prolonged release of the active ingredients in the small intestine (duodenum, ileum, jejunum) can also be achieved by encasing the active agents, or by encasing hydrophilic, water-swellable polymers containing the active agents, in an enteric (acid-resistant) film. One class of acid-resistant agents suitable for this purpose is that disclosed in Eury et al., U.S. Pat. No. 5,316,774 ("Blocked Polymeric Particles Having Internal Pore Networks for Delivering Active Substances to Selected Environments"). The formulations disclosed in this patent consist of porous particles whose pores contain an active ingredient and a polymer acting as a blocking agent that degrades and releases the active ingredient upon exposure to either low or high pH or to changes in ionic strength. The most effective enteric materials include polyacids having a $PK_a$ of from about 3 to 5. Examples of such materials are fatty acid mixtures, methacrylic acid polymers and copolymers, ethyl cellulose, and cellulose acetate phthalates. Specific examples are methacrylic acid copolymers sold under the name EUDRAGIT®, available from Rohm Tech, Inc., Maiden, Massachusetts, USA; and the cellulose acetate phthalate latex AQUATERIC®, available from FMC Corporation, New York, N.Y., USA, and similar products available from Eastman-Kodak Co., Rochester, N.Y., USA.

Acid-resistant films of these types are particularly useful in confining the release of active agents to the post-gastric environment. Acid-resistant films can be applied as coatings over individual particles of the components of the formulation, with the coated particles then optionally compressed into tablets. An acid-resistant film can also be applied as a layer encasing an entire tablet or a portion of a tablet where each tablet is a single unit dosage form.

The dosage forms of the invention optionally include one or more suitable and pharmaceutically acceptable excipients, such as ethyl cellulose, cellulose acetate phthalates, mannitol, lactose, starch, magnesium stearate, sodium saccharin, talcum, glucose, sucrose, carbonate, and the like. These excipients serve a variety of functions, as indicated above, as carriers, vehicles, diluents, binders, and other formulating aids. In general, the dosage forms of this invention include powders, liquid forms, tablets or capsules.

In certain embodiments of the invention, the dosage form is a substantially homogeneous single layer tablet that releases all of its components into the stomach upon ingestion.

In certain other embodiments of the invention, the dosage form is a tablet in which the active agents are protected by an acid-resistant coating for release only in the intestine, and optionally in a sustained-release manner over a period of time.

The dosage forms of this invention can be formulated for administration at rates of two or more unit dosage forms per day. Unit dosage forms to be taken three to four times per day for immediate release tablets are preferred. Unit dosage forms to be taken once or twice daily for controlled (sustained) release tablets are preferred.

The following examples are not intended to enumerate the entire spectrum of formulations possible for the invention, but are offered for purposes of illustration only.

Example 1 L-Arginine Ascorbate

IMMEDIATE RELEASE

L-Arginine Ascorbate

| Ranges in milligrams per day | Compound | L-Lysine | Ascorbate |
|---|---|---|---|
| Preferred | 213 | 83 | 75 |
| To | 7113 | 2761 | 2500 |
| Most Preferred | 711 | 276 | 250 |
| To | 2845 | 1104 | 1000 |

SINGLE LAYER UNIT DOSAGE FORM FOR:

| | tabs/day | | |
|---|---|---|---|
| L-Arginine Ascorbate | 3.00 | | Per day |

TABLET WEIGHT

| | mg/day | Mg | mcg |
|---|---|---|---|
| 474 | 1423 | L-Arginine 552 | |

FOR IMMEDIATE RELEASE IN THE STOMACH   100%

| | | % of formula | Milligrams | | Mg | mcg |
|---|---|---|---|---|---|---|
| $C_{12}H_{21}O_8N_4$ | L-Arginine Ascorbate | 73.93% | 1051.77 | Arg Excipients | Ascorbate | 500 |
| $Mg(C_{18}H_{35}O_2)_2$ | Magnesium Stearate | 0.76% | 10.84 | Mag | Stearate | 10.4 |
| ... | Starch | 25.31% | 360.00 | | Starch (25%) | 360 |

AQUEOUS FILM

SUSTAINED RELEASE

L-Arginine Ascorbate

| Ranges in milligrams per day | Compound | L-Lysine | Ascorbate |
|---|---|---|---|
| Preferred | 199 | 83 | 75 |
| To | 6643 | 2761 | 2500 |
| Most Preferred | 664 | 276 | 250 |
| To | 2657 | 1104 | 1000 |

SINGLE LAYER UNIT DOSAGE FORM FOR:

| | tabs/day | | |
|---|---|---|---|
| L-Arginine Ascorbate | 2.00 | | Per day |

TABLET WEIGHT

| | mg/day | Mg | mcg |
|---|---|---|---|
| 664 | 1329 | L-Arginine 552 | |

FOR SUSTAINED RELEASE   100%

| | | % of formula | Milligrams | | Mg | mcg |
|---|---|---|---|---|---|---|
| $C_{12}H_{21}O_8N_4$ | L-Arginine Ascorbate | 79.16% | 1051.77 | Arg Excipients | Ascorbate | 500 |
| $Mg(C_{18}H_{35}O_2)_2$ | Magnesium Stearate | 0.75% | 9.91 | Mag | Stearate | 9.5 |
| ... | Polymer ($H_2O$ Sol, Cellulose) | 20.10% | 267.00 | | Polymer (20%) | 267 |

ACID RESISTANT FILM

Example 2 Magnesium L-Arginate

IMMEDIATE RELEASE

Magnesium Arginate

| Ranges in milligrams per day | Compound | Magnesium | Arginate |
|---|---|---|---|
| Preferred | 181 | 9 | 125 |
| to | 4539 | 221 | 3125 |
| Most Preferred | 363 | 18 | 250 |
| to | 1816 | 88 | 1250 |

SINGLE LAYER UNIT DOSAGE FORM FOR:

| | tabs/day | | |
|---|---|---|---|
| Magnesium Arginate | 3.00 | | Per day |
| TABLET WEIGHT | mg/day | | Mg  mcg |
| 339 | 1017 | Magnesium | 49 |
| FOR IMMEDIATE RELEASE IN THE STOMACH | 100% | | |
| | % of formula  milligrams | | Mg  mcg |
| $Mg(C_6H_{13}N_4O_2)_2$  Magnesium L-Arginate | 73.67%  749.12 | Mag       Arginate | 700 |
| | | excipients | |
| $Mg(C_{18}H_{35}O_2)_2$  Magnesium Stearate | 0.76%  7.72 | Mag       Stearate | 7.4 |
| ...  Starch | 25.57%  260.00 | Starch (25%) | 260 |

AQUEOUS FILM

SUSTAINED RELEASE

Magnesium L-Arginate

| Ranges in milligrams per day | Compound | Magnesium | Arginate |
|---|---|---|---|
| Preferred | 170 | 9 | 125 |
| to | 4269 | 221 | 3125 |
| Most Preferred | 341 | 18 | 250 |
| to | 1708 | 88 | 1250 |

SINGLE LAYER UNIT DOSAGE FORM FOR:

| | tabs/day | | |
|---|---|---|---|
| Magnesium L-Arginate | 1.00 | | Per day |
| TABLET WEIGHT | mg/day | | Mg  mcg |
| 956 | 956 | Magnesium | 49 |
| FOR SUSTAINED RELEASE | 100% | | |
| | % of formula  milligrams | | Mg  mcg |
| $Mg(C_6H_{13}N_4O_2)_2$  Magnesium L-Arginate | 78.33%  749.12 | Mag       Arginate | 700 |
| | | excipients | |
| $Mg(C_{18}H_{35}O_2)_2$  Magnesium Stearate | 0.76%  7.30 | Mag       Stearate | 7.0 |
| ...  Polymer (H$_2$O Sol, Cellulose) | 20.91%  200.00 | Polymer (20%) | 200 |

ACID RESISTANT FILM

Example 3 Zinc L-Arginate

IMMEDIATE RELEASE

| Zinc L-Arginate | | | | |
|---|---|---|---|---|
| Ranges in milligrams per day | Compound | Zinc | L-Arginine | |
| Preferred | 13 | 1.5 | 8 | |
| to | 1064 | 125 | 662 | |
| Most Preferred | 39 | 5 | 24 | |
| to | 428 | 50 | 266 | |

| SINGLE LAYER UNIT DOSAGE FORM FOR: | | tabs/day | | |
|---|---|---|---|---|
| Zinc L-Arginate | | 3.00 | | Per day |
| TABLET WEIGHT | | mg/day | | Mg     mcg |
| 99 | | 297 | | Zinc     35 |
| FOR IMMEDIATE RELEASE IN THE STOMACH | 100% | | | |
| | % of formula | milligrams | | Mg     mcg |
| $ZnC_6H_{13}N_4O_2$  Zinc L-Arginate | 73.99% | 219.92 | Zn    L-Arginine 185 excipients | |
| $Mg(C_{18}H_{35}O_2)_2$  Magnesium Stearate | 0.77% | 2.29 | Mag    Stearate   2.2 | |
| . . .  Starch | 25.23% | 75.00 | Starch (25%)   75 | |

AQUEOUS FILM

SUSTAINED RELEASE

| Zinc L-Arginate | | | | |
|---|---|---|---|---|
| Ranges in milligrams per day | Compound | Zinc | L-Arginine | |
| Preferred | 12 | 1.5 | 8 | |
| to | 995 | 125 | 662 | |
| Most Preferred | 36 | 5 | 24 | |
| to | 400 | 50 | 266 | |

| SINGLE LAYER UNIT DOSAGE FORM FOR: | | tabs/day | | |
|---|---|---|---|---|
| Zinc L-Arginate | | 1.00 | | Per day |
| TABLET WEIGHT | | mg/day | | Mg     mcg |
| 278 | | 278 | | Zinc     35 |
| FOR SUSTAINED RELEASE | 100% | | | |
| | % of formula | milligrams | | Mg     mcg |
| $ZnC_6H_{13}N_4O_2$  Zinc L-Arginate | 79.11 | 219.92 | Zn    L-Arginine 185 excipients | |
| $Mg(C_{18}H_{35}O_2)_2$  Magnesium Stearate | 0.75% | 2.09 | Mag    Stearate   2.0 | |
| . . .  Polymer (H₂O Sol, Cellulose) | 20.14% | 56.00 | Polymer (20%)   56 | |

ACID RESISTANT FILM

Example 4 Copper L-Arginate

IMMEDIATE RELEASE

Copper L-Arginate

| Ranges in milligrams per day | Compound | Cu | L-Arginine |
|---|---|---|---|
| Preferred | 1 | 0.15 | 0.4 |
| to | 38 | 7.5 | 21 |
| Most Preferred | 2 | 0.5 | 1 |
| to | 15 | 3.0 | 8 |

SINGLE LAYER UNIT DOSAGE FORM FOR:

| | tabs/day | | Per day | |
|---|---|---|---|---|
| Copper L-Arginate | 3.00 | | | |
| TABLET WEIGHT | mg/day | | Mg | mcg |
| 5 | 15 | | Cu | 3 |
| FOR IMMEDIATE RELEASE IN THE STOMACH 100% | | | | |
| | % of formula | milligrams | Mg | mcg |
| $CuC_6H_{13}N_4O_2$   Copper L-Arginate | 74.11 | 11.21 | Cu    L-Arginine   8.2 excipients | |
| $Mg(C_{18}H_{35}O_2)_2$   Magnesium Stearate | 0.76% | 0.11 | Mag    Stearate   0.11 | |
| ...   Starch | 25.13% | 3.80 | Starch (25%)   3.80 | |

AQUEOUS FILM

SUSTAINED RELEASE

Copper L-Arginate

| Ranges in milligrams per day | Compound | Cu | L-Arginine |
|---|---|---|---|
| Preferred | 1 | 0.15 | 0.4 |
| to | 36 | 7.5 | 21 |
| Most Preferred | 2 | 0.5 | 1 |
| to | 14 | 3.0 | 8 |

SINGLE LAYER UNIT DOSAGE FORM FOR:

| | tabs/day | | Per day | |
|---|---|---|---|---|
| Copper L-Arginate | 1.00 | | | |
| TABLET WEIGHT | mg/day | | Mg | mcg |
| 14 | 14 | | Cu | 3 |
| FOR SUSTAINED RELEASE 100% | | | | |
| | % of formula | milligrams | Mg | mcg |
| $CuC_6H_{13}N_4O_2$   Copper L-Arginate | 78.28% | 11.21 | Cu    L-Arginine   8.2 Excipients | |
| $Mg(C_{18}H_{35}O_2)_2$   Magnesium Stearate | 0.76% | 0.11 | Mag    Stearate   0.11 | |
| ...   Polymer ($H_2O$ Sol, Cellulose) | 20.05% | 3.00 | Polymer (20%)   3.00 | |

ACID RESISTANT FILM

Types of Utility and Methods of Administration

The compositions and dosage forms of the invention are useful for beneficially modifying the conditions and functions that affect a variety of acute and chronic clinical conditions; particularly those associated with endothelial dysfunction and aging. A partial list of diagnoses or findings caused or worsened by endothelial diseases would include, among others:

| | |
|---|---|
| Systemic or chronic essential hypertension | Atherosclerosis |
| Cerebral vascular disease | Diabetes Mellitus and Insulin resistance |
| Chronic open angle glaucoma | Impotency |
| Depressed wound healing | Coronary artery disease |
| Acute and chronic inflammation | Macular degeneration |
| Alzheimer's disease | Parkinson's disease |
| Aging | |

As reviewed in this document, the ingredients of the invention have actions which are functionally additive or complementary and which favorably influence the status of the above clinical problems. These actions include:

Increases in glutathione and its effects
Inhibition of aldose reductase (reduction of sorbitol)
Limitation of endothelial dysfunction
Improvement of impaired vasodilatation
Reduction of defective AcH responses
Limitation of VSMC hypertrophy
Modulation of calcium signaling
Reduction of lipid peroxidation
Reduction of free radicals
Protection/rejuvenation of vitamin E and α-lipoic acid
Platelet stabilization
Improvements in blood fluidity and laminar flow
Reduction of vasoconstriction Reduction of neural glutamate excitotoxicity The carefully chosen active ingredients of the invention act in a well-defined, uniquely efficient biochemical partnership to ensure that vascular risk factors are clinically reduced. The resulting improvement in systemic and in ocular vascular health, especially in vascular endothelial health, maximizes the potential for success of current therapeutics and minimizes the potential that present treatment regimes will fail because of neglected, unrecognized or unappreciated vascular inadequacy. The age group most commonly first diagnosed with vascular, glutamate excitotoxic disease or chronic ocular disease also is a chronological group moving into the physiological arena of reduced cellular efficiency secondary to age; at the same time it faces a concomitant increasing incidence of other chronic diseases.

By directly providing absorbable L-arginine, the critical precursor of NO, the invention positively influences the NO/ET-1 balance, modulates a controlled reduction in $Ca^{+2}$ cellular inflow via physiological $Ca^{+2}$ channel blockade, reduces platelet aggregation, lowers microviscosity and improves laminar flow, reduces the inflammatory risks associated with local free radicals such as hydroxyls or superoxide, and limits the rate of oxidation of low density lipids. The invention provides significant protection for patients with reduced levels of cNOS or eNOS and their product, NO. This is associated with the efficient and unique concurrent delivery of appropriately balanced amounts of $Mg^{+2}$, $Cu^{+2}$, and $Zn^{+2}$, which are complementary in their physiological behavior. As a result the invention reduces various risks associated with unbalanced vasoactive disease in general and of risks associated with hypertension, atherosclerosis, diabetes mellitus, of progressive visual field loss and eventual optic nerve atrophy commonly associated with chronic glaucoma, the central visual loss associated with macular degeneration and various clinical presentations associated with neurological excitotoxicity.

In some cases the invention incorporates the ascorbate radical as an integral antioxidant component of the metal-loarginate molecule, bringing to the invention a logical clinical efficiency and control not otherwise currently available.

Epidemiological studies have confirmed repeatedly that inadequate dietary intake of $Mg^{+2}$, $Zn^{+2}$ and $Cu^{+2}$ is common in the general public and is especially rampant in elderly, institutionalized patients, diabetics, alcoholics and cigarette smokers. By combining both an important metal ion and L-arginine in a single compound, the invention ensures appropriate nutritional balancing of both moieties.

Other patients have disturbances of reduced absorption or abnormal loss of these critical biofactors (e.g., in the hypochlorhydria of age, diabetes, renal pathology, gastrointestinal pathology, etc.) The distribution of chronic vascular disease and of glaucoma among these particular groups not only is no less than in the general public, but is increased. By favorably modifying common physiological conditions and functions, the invention is especially useful in reducing the risk of harm associated with the vasculopathy of these clinical states. It may be expected that an improvement in vascular health will not only be generally beneficial to these clinical subgroups but will also provide a specific reduction in risk for the chronic glaucoma or macular degeneration patient who is inherently so much at risk of vascular-induced visual loss and blindness.

Patients with Parkinson's disease and Alzheimer's disease, most likely associated with central glutamate neural excitotoxicity, will benefit from the invention.

The foregoing is offered primarily for purposes of illustration. It will be readily apparent to those skilled in the art that the proportions, materials, formulation procedures, administration protocols and other parameters of this invention may be further modified or substituted in various ways without departing from the spirit and scope of the invention.

We claim:

1. A unit dosage form for the correction of vascular insufficiency and conditions giving rise thereto, said dosage form having a clinically effective amount of a metal L-arginate complex of the formula $$(Arg) M X$$

in which:

Arg is a member selected from the group consisting of L-arginine and bis-L-arginine;

M is a metal ion selected from the group consisting of $Mg^{+2}$, $Cu^{+2}$ and $Zn^{+2}$; and X is an anion selected from the group consisting of hydroxide, halide, sulfate, phosphate, acetate, ascorbate and bis-ascorbate.

2. A method for ameliorating a condition in a subject giving rise to or associated with a clinical diagnosis or finding selected from the group consisting of chronic essential hypertension, cerebral vascular disease, chronic open angle glaucoma, depressed wound healing, acute and chronic inflammation, Alzheimer's disease, atherosclerosis, diabetes mellitus and insulin resistance, impotency, coronary artery disease, aging, and Parkinson's disease, said method comprising administering to said subject a metal L-arginate complex in an amount effective in reducing said condition, said metal L-arginate complex having the formula $$(Arg) M X$$

in which:

Arg is a member selected from the group consisting of L-arginine and bis-L-arginine;

M is a metal ion selected from the group consisting of $Mg^{+2}$, $Cu^{+2}$ and $Zn^{+2}$; and X is an anion selected from the group consisting of hydroxide, halide, sulfate, phosphate, acetate, ascorbate and bis-ascorbate.

* * * * *